(12) United States Patent
Carey et al.

(10) Patent No.: US 9,558,322 B2
(45) Date of Patent: Jan. 31, 2017

(54) SECURE COMPUTING SYSTEMS AND METHODS

(71) Applicant: Intertrust Technologies Corporation, Sunnyvale, CA (US)

(72) Inventors: W. Knox Carey, Mountain View, CA (US); Jarl A. Nilsson, Mountain View, CA (US); Bart Grantham, Mountain View, CA (US)

(73) Assignee: Intertrust Technologies Corporation, Sunnyvale, CA (US)

( * ) Notice: Subject to any disclaimer, the term of this patent is extended or adjusted under 35 U.S.C. 154(b) by 0 days.

(21) Appl. No.: 14/702,632

(22) Filed: May 1, 2015

(65) Prior Publication Data

US 2015/0317490 A1  Nov. 5, 2015

Related U.S. Application Data

(60) Provisional application No. 61/987,365, filed on May 1, 2014, provisional application No. 62/077,691, filed on Nov. 10, 2014.

(51) Int. Cl.
| | |
|---|---|
| *G06F 7/04* | (2006.01) |
| *G06F 17/30* | (2006.01) |
| *H04N 7/16* | (2011.01) |
| *G06F 19/28* | (2011.01) |
| *G06F 21/62* | (2013.01) |
| *G06F 19/18* | (2011.01) |

(52) U.S. Cl.
CPC ............... *G06F 19/28* (2013.01); *G06F 19/18* (2013.01); *G06F 21/62* (2013.01); *G06F 21/6245* (2013.01)

(58) Field of Classification Search
CPC .......... G06F 19/28; G06F 19/18; G06F 21/62; G06F 21/6245
USPC ............................................................ 726/26
See application file for complete search history.

(56) References Cited

U.S. PATENT DOCUMENTS

| | | | |
|---|---|---|---|
| 2005/0026117 A1 | 2/2005 | Judson et al. | |
| 2005/0149726 A1* | 7/2005 | Joshi ....................... | G06F 21/51 713/164 |
| 2005/0165881 A1* | 7/2005 | Brooks ................. | G06F 9/5027 709/200 |
| 2008/0081957 A1 | 4/2008 | Jung et al. | |
| 2008/0281529 A1 | 11/2008 | Tenenbaum et al. | |

(Continued)

OTHER PUBLICATIONS

Yuri Demchenko ; Addressing Big Data Challenges for Scientific Data Infrastructure; University of Amsterdam year: 2012; p. 1-4.*

(Continued)

*Primary Examiner* — Monjour Rahim
(74) *Attorney, Agent, or Firm* — Finnegan, Henderson, Farabow, Garrett & Dunner LLP

(57) ABSTRACT

The present disclosure relates to systems and methods for facilitating trusted handling of genomic and/or other sensitive information. Certain embodiments may use a virtualized execution environment to execute code and/or programs that wish to access and/or otherwise use genomic and/or other sensitive information. In some embodiments, data requests from the code and/or programs may be routed through a transparent data access proxy configured to transform requests and/or associated responses to protect the integrity of the genomic and/or other sensitive information.

20 Claims, 11 Drawing Sheets

(56) References Cited

U.S. PATENT DOCUMENTS

| | | | |
|---|---|---|---|
| 2010/0115530 A1* | 5/2010 | Ahmad | G06F 9/461 718/108 |
| 2011/0047189 A1 | 2/2011 | Will et al. | |
| 2013/0096943 A1 | 4/2013 | Carey et al. | |
| 2014/0181819 A1* | 6/2014 | Mickens | G06F 21/53 718/100 |

OTHER PUBLICATIONS

Callaway, E.; "Global Genomic Data-Sharing Effort Kicks Off"; Nature News; Mar. 6, 2014; pp. 1-2.
Gymrek, M. et al.: "Identifying Personal Genomes by Surname Inference"; Science, vol. 339, No. 6117; Jan. 18, 2013; pp. 321-324.
Homer, N. et al.; "Resolving individuals contributing trace amounts of DNA to highly complex mixtures using high-density SNP genotyping microarrays"; PLoS Genetics; vol. 4,. No. 8; Aug. 2008; pp. 1-9.
Kolata, G.; "Poking Holes in Genetic Privacy"; New York Times, Jun. 16, 2013; pp. 1-3.
Lemke, A.A. et al.; "Public and Biobank Participant Attitudes toward Genetic Research Participation and Data Sharing"; Public Health Genomics; vol. 13; Jan. 15, 2010; pp. 368-377.
Lunshof, J. et al.; "From Genetic Privacy to Open Consent"; Nature Reviews | Genetics; vol. 9; May 2008; pp. 406-411.
Nyholt, D. et al.; "On Jim Watson's *APOE* status: genetic information is hard to hide"; European Journal of Human Genetics; vol. 17, No. 2; Feb. 2009; pp. 147-149.
Sankararaman, S. et al.; "Genomic privacy and limits of individual detection in a pool"; Nature Genetics; vol. 41, No. 9; Sep. 2009; pp. 965-967.
International Search Report and Written Opinion dated Aug. 4, 2015; PCT Application PCT/US2015/028949.

\* cited by examiner

```
import json, sys, urllib def geneserver_request(api_path):
    url = 'http://geneserver.genecloud.com/%s' % api_path
    http_handle = urllib.urlopen(url)
    return http_handle.read()

def query_gene_exon(genome_id, gene_name, exon):
    return geneserver_request('genome/%s/variant/gene/%s/exon/%s' %
        (genome_id, gene_name, exon))

if __name__ == "__main__":
    genome_id = sys.argv[1]
    results = []
    for (gene, exons) in [["PIK3CA", [1, 5, 7, 9, 20]], ["PTEN", [5, 6, 7, 8]]]:
        for exon in exons:
            result_raw = query_gene_exon(genome_id, gene, exon)
            if result_raw is not False:
                result = json.loads(result_raw)
                if 'variants' in result:
                    results += result['variants']
    print json.dumps({'variants': results})
```

Figure 4

```
GET /genome/5685c028bf7811e3a21a12470ec1d3b5/variant/rsid/rs1933437 HTTP/1.1
Host: geneserver.genecloud.com Content-Type: text/html; charset=utf-8
Content-Length: 266
Date: Sun, 27 Apr 2014 23:48:30 GMT {"variants": [
 {"annotations": [
   {"clinical_annotation": "T227M", "exon_rank": 6, "gene_name": "FLT3",
    "rs_id": "rs1933437", "ref_gt": "G", "var_gt": "A",
    "hgvs_annotation": "FLT3 NM_004119.2: c.680G>A (p.Thr227Met)"}],
  "chromosome": "chr13", "position": "28624294"}]}
```

SECURE COMPUTING SYSTEMS AND METHODS

RELATED APPLICATIONS

This application claims the benefit of priority under 35 U.S.C. §119(e) to U.S. Provisional Patent Application No. 61/987,365, filed May 1, 2014, and entitled "SECURE COMPUTING SYSTEMS AND METHODS", and to U.S. Provisional Patent Application No. 62/077,691, filed Nov. 10, 2014, and entitled "SECURE COMPUTING SYSTEMS AND METHODS", both of which are hereby incorporated by reference in their entireties.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent files or records, but otherwise reserves all copyright rights whatsoever.

SUMMARY

The present disclosure relates generally to systems and methods for facilitating trusted handling of information. More specifically, but not exclusively, the present disclosure relates to systems and methods for enabling secure, governed, and/or audited use of genomic, medical, healthcare, bioinformatics, and/or other sensitive information.

Data fuels scientific discovery, and technology that restricts access to data may impede scientific process. This risk is particularly acute in healthcare systems, where data that sits idle is data that may not be used to treat patients and/or develop new technologies and/or cures. Healthcare data, however, is sensitive in nature, and its public disclosure may have certain detrimental effects. For example, genomic information can reveal a significant amount of detail regarding health status and disease risk—not only for a patient, but for the patient's relatives as well. Even in an anonymized form, genomic information may be susceptible to attacks that may compromise patient privacy and/or the privacy of other associated individuals. Accordingly, balancing the goals of increasing the amount of genomic data available for use by researchers and/or other healthcare providers while preserving privacy of patients and/or interested individuals and preventing compromising attacks can prove difficult.

Under some access models, researchers and/or other entities that may wish to access genomic and/or other sensitive data may be carefully screened. Following successful screening, however, the researchers and/or entities may be given unfettered and/or relatively unrestricted access to the genomic and/or other sensitive data under the assumption that they can be trusted to respect the privacy interests of associated subjects (e.g., patients). Such an approach, however, may not address the inherent intransitivity of trust. For example, such access models may not specifically address whether a trusted and/or screened researcher may e-mail a patient's personal data to a colleague whom they trust, whether the researcher can legitimately e-mail a subset of the information, and, if so, how large of a subset would be acceptable, what the ethical obligations of the researcher are with respect to managing the computing infrastructure on which the patient's personal data is stored, and/or the like.

A potential problem with this conventional access model is that it may expect users to enforce relatively complex policies that govern the use of data. Once information has been revealed and/or otherwise provided to a recipient (e.g., a researcher), the burden is placed on the recipient to act with discretion in protecting the privacy of the data, a requirement that may be in conflict with the recipient's desire to accomplish a particular scientific or research task that may be more readily achieved by sharing the personal data, and/or that may be beyond the recipient's technical capabilities.

Systems and methods are described herein that ameliorate some or all of these problems. Consistent with embodiments disclosed herein, a data service may be used to provide stronger security and/or privacy functionality in connection an application (e.g., with a model-view-controller ("MVC") web-application and/or the like) that may interact with sensitive data (e.g., genomic or other medical or bioinformatics data). In certain embodiments, the disclosed systems and methods may address privacy concerns relating to the use of genomic and/or other sensitive data and may mitigate the potential for compromising attacks involving such data. In further embodiments, the disclosed systems and methods can be used to enable secure and/or policy-based access to and/or use of sensitive data. Among other things, embodiments of the disclosed systems and methods may facilitate policy-based governance of access to and/or use of genomic and/or other sensitive data (e.g., distribution, analysis, etc.), improved interaction with and/or use of distributed genomic and/or other sensitive data, reduced user involvement in genomic and/or other sensitive data workflow processes, and/or the like.

BRIEF DESCRIPTION OF THE DRAWINGS

The inventive body of work will be readily understood by referring to the following detailed description in conjunction with the accompanying drawings, in which:

FIG. 4 illustrates an exemplary program for use in connection with a data service consistent with embodiments of the present disclosure FIG. 5 illustrates an exemplary exchange in connection with a data access request via an application programming interface consistent with embodiments of the present disclosure.

DETAILED DESCRIPTION

Figure 1:
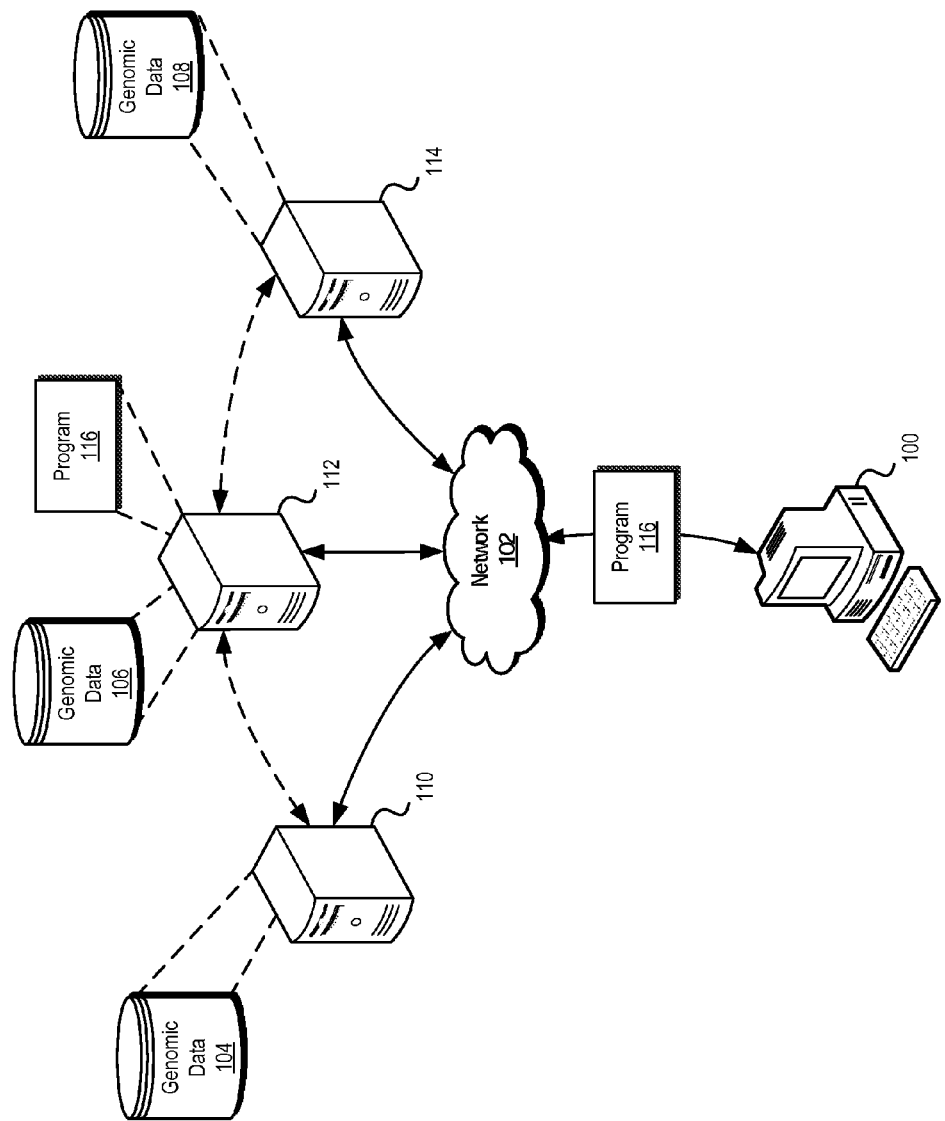
FIG. 1 illustrates an exemplary ecosystem for storage, management, and processing of sensitive data consistent with embodiments of the present disclosure.

A detailed description of systems and methods consistent with embodiments of the present disclosure is provided below. While several embodiments are described, it should be understood that the disclosure is not limited to any one embodiment, but instead encompasses numerous alternatives, modifications, and equivalents. For example, while, for purposes of illustration, a number of examples have been provided in the context of genomic data, it will be appreciated that the systems and methods disclosed herein are not limited to that context, and could be readily used with other forms of sensitive data. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

Various embodiments of the disclosure may be understood by reference to the drawings, wherein like parts may be designated by like numerals in certain instances. Components of the disclosed embodiments, as generally described and illustrated in the figures herein, could be arranged and designed in a wide variety of different configurations. Thus, the following detailed description is not intended to limit the scope of the disclosure, as claimed, but is merely representative of possible embodiments of the disclosure. In addition, the steps of any method disclosed herein do not necessarily need to be executed in any specific order, or even sequentially, nor need the steps be executed only once, unless otherwise specified.

Systems and methods are presented that facilitate secure, governed, and/or audited use of genomic and/or other sensitive information. In certain embodiments, the disclosed systems and methods can be used to enable policy-based governance of access to and/or use of sensitive data, improve interaction with and/or use of distributed data, reduce user involvement in data workflow processes, and/or the like. Consistent with embodiments disclosed herein, a data service may provide a framework for trusted cloud services that store and/or analyze genetic sequences and/or other medical or bioinformatic information. Among other things, embodiments of the disclosed data service may address issues of privacy with respect to genomic or other sensitive data by allowing researchers and clinicians to interact with data through computer programs (e.g., trusted analytics), that may be managed in a variety of ways according to enforced policies determined by the various stakeholders in the data. It will be appreciated that these systems and methods are novel, as are many of the components, systems, and methods employed therein.

In certain embodiments, the systems and methods described herein can, for example, be used in connection with digital rights management ("DRM") technologies such as those described in commonly assigned U.S. Pat. No. 8,776,216, entitled "Digital Rights Management Engine Systems and Methods," filed Oct. 18, 2006 ("the '216 patent"), service orchestration and DRM technologies such as those described in commonly assigned U.S. Pat. No. 8,234,387, entitled "Interoperable Systems and Methods for Peer-to-Peer Service Orchestration", filed Jun. 7, 2004 ("the '387 patent"), information governance technologies such as those described in commonly assigned, co-pending U.S. patent application Ser. No. 13/444,624, entitled "Information Security Systems and Methods", filed Apr. 11, 2012 ("the '624 application"), information processing technologies such as those described in commonly assigned, co-pending U.S. patent application Ser. No. 13/654,349, entitled "Systems and Methods for Protecting and Governing Genomic and Other Information", filed Oct. 17, 2012 ("the '349 application") and U.S. patent application Ser. No. 14/260,714, entitled "Bioinformatic Processing Systems and Methods", filed Apr. 24, 2014 ("the '714 application"), and/or computation technologies such as those described in commonly assigned, co-pending U.S. patent application Ser. No. 13/840,793, entitled "Distributed Computation Systems and Methods," filed Mar. 15, 2013 ("the '793 application") (the contents of the '216 patent, the '387 patent, the '624 application, the '349 application, the '714 application, and the '793 application are hereby incorporated by reference in their entireties), as well as in other contexts.

Data Processing Ecosystem

FIG. 1 illustrates an exemplary ecosystem for storage, management, and processing of genomic data 104-108 consistent with embodiments of the present disclosure. As used herein, the terms "genomic data" and/or "genomic information" may generally refer to data expressing, representing, and/or derived from the entirety or a portion of a genome or genome sequence. This data may include, without limitation, information encoded in chemical structures such as DNA, mRNA, and proteins as well as related information such as methylation status. As used herein the term "genome" may refer to an organism's hereditary information. A genome may be encoded in DNA or RNA, and may be represented as mRNA or as protein sequences derived from these nucleic acid sequences. The term "genome" may include both genes and non-coding sequences. When applied to a specific organism, the term "genome" can refer to genomic data from normal cells—including mitochondrial DNA—and also genomic data from related cells such as tumors and other organisms of the microbiome. Although some embodiments of the disclosed systems and methods are discussed herein in connection with genomic data, it will be appreciated that the disclosed systems and methods may also be used in connection with any other suitable information, including, for example, other types of bioinformatics data (e.g. transcriptome, connectome, incidentalome, etc.) and/or other personal, private, and/or otherwise sensitive information.

Referring to FIG. 1, a client system 100 may provide a variety of functions that allow a user (e.g., a researcher or clinician) to process, analyze, or otherwise interact with genomic data 104-108. In certain embodiments, the client system 100 may be communicatively coupled with one or more data storage and/or processing systems 110-114 via a network 102. In some embodiments, at least some of the one or more data storage and/or processing systems 110-114 may be communicatively coupled with each other via the network 102 and/or through one or more other communication channels.

The one or more data storage and/or processing systems 110-114 may, among other things, be configured to store and/or manage genomic data 104-108 and/or interact with the client system 100 in connection with the same. Consistent with the disclosed embodiments, the one or more data storage and/or processing systems 110-114 may be associated with a genomic data service, providing a framework for trusted cloud services that store and/or analyze genetic sequences and/or other information.

The client system 100 may interact with information stored by the one or more data storage and/or processing systems 110-114 to perform various operations thereon. For example, the client system 100 may provide the one or more data storage and/or processing systems 110-114 with one or more programs, applications, code, and/or processes (e.g., program 116) configured to interact with genomic data 104-108 stored thereon. The one or more data storage and/or processing systems 110-114 may execute such programs, applications, code, and/or processes in a trusted and/or policy-managed manner, and may communicate associated results to the client system 100.

In some embodiments, the data storage and/or processing systems 110-114 may interact with one another directly to compute a result. For example, the client system 100 may provide one of the data storage and/or processing systems 110-114 with one or more programs, applications, code, and/or processes (e.g., program 116). This data storage and/or processing system may evaluate whether it has access to the data required by the program, and forward the program to other data storage and/or processing systems as may be necessary or desirable, receiving the computed results directly from the other data storage and/or processing systems, potentially performing additional processing on the results returned, and then returning the results to client system 100.

The network 102 may comprise any suitable combination of network communication devices and/or channels and may use any suitable communication protocols and/or technologies to facilitate communication between the client system 100, the data storage and/or processing systems 110-114, and/or one or more other systems. For example, the network 102 may comprise the Internet, a local area network, a virtual private network, or any other communication network or combination thereof. For example, in some embodiments, the network 102 may comprise a wireless carrier system, such as a personal communications system ("PCS"), and/or any other suitable communication system incorporating any suitable communications technologies, standards, and/or protocols. In further embodiments, the network 102 may comprise an analog mobile communications network and/or a digital mobile communications network utilizing, for example, code division multiple access ("CDMA"), Global System for Mobile Communications or Groupe Speciale Mobile ("GSM"), frequency division multiple access ("FDMA"), time divisional multiple access ("TDMA"), or orthogonal frequency division multiple access (OFDMA) standards. In certain embodiments, the network 102 may incorporate one or more satellite communication links. In yet further embodiments, the network 102 may use IEEE's 802.11 standards, Bluetooth®, ultra-wide band ("UWB"), Zigbee®, and/or any other suitable technology or technologies.

The client system 100 and/or the data storage and/or processing systems 110-114 may comprise a variety of computing devices and/or systems, including, for example, laptop computer systems, desktop computer systems, sever computer systems, distributed computer systems, smartphones, tablets, and/or the like. It will be appreciated that any suitable configuration of computing systems and storage media could be used in connection with systems 100, 110-114, including without limitation, a single server or cluster of servers, or a distributed collection of heterogeneous computer systems connected by a variety of networks (e.g., such as the Internet, public and/or private networks, and/or the like).

In certain embodiments, the client system 100 and/or the data storage and/or processing systems 110-114 may comprise at least one processor system configured to execute instructions stored on an associated non-transitory computer-readable storage medium. As discussed in more detail below, the client system 100 and/or the data storage and/or processing systems 110-114 may further comprise a secure processing unit ("SPU") configured to perform sensitive operations such as trusted credential and/or key management, secure policy management, and/or other aspects of the systems and methods disclosed herein. The client system 100 and/or the data storage and/or processing systems 110-114 may further comprise software and/or hardware configured to enable electronic communication of information between the devices and/or systems 100, 110-114 via the network 102 using any suitable communication technology and/or standard.

The data storage and/or processing systems 110-114 may be configured to store, manage, process, distribute, and/or update certain data 104-108 stored thereon. In certain embodiments, the data storage and/or processing systems 110-114 may be associated with one or more processing domains, jurisdictions, organizations, institutions, users, locations and/or the like. As an example, data storage and/or processing system 110 and associated data 104 may be associated with a research institution, data storage and/or processing system 112 and associated data 106 may be associated with a jurisdiction that does not allow distribution of data 106 from the jurisdiction, and data storage and/or processing system 114 and associated data 108 may be associated with a business organization offering data 108 as a data product for clinical and/or research purposes. In certain embodiments, the data storage and/or processing systems 110-114 may be associated with one or more cloud-based systems for the trusted storage and analysis of the data, and may incorporate embodiments of the disclosed data service and/or certain systems and methods disclosed, for example, in connection with the '349 application.

As discussed above, an application executing on the client system 100 may enable a user of the system to interact with the one or more data storage and/or processing systems 110-114 in connection with performing various workflow processes and/or analyses using the data 104-108. For example, in certain embodiments, the client system 100 may be configured to issue requests/queries to programs, applications, code, and/or processes (e.g., program 116) executed on the data storage and/or processing systems 110-114 directing the data storage and/or processing systems 110-114 to perform certain processes and/or operations using data 104-108 managed thereon. Consistent with embodiments disclosed herein, the one or more data storage and/or processing systems 110-114 may execute such programs, applications, code, and/or processes in a trusted and/or policy-managed manner, and may communicate associated results to the client system 100. Results of the processes and/or operations may be returned to the client system 100 from the associated data storage and/or processing systems 110-114.

In some embodiments, the one or more data storage and/or processing systems 110-114 may include varying levels of hardware and/or software security hardening based on the sensitivity of the data 104-108 stored thereon. For example, genomic data that does not include information associating particular genetic sequences with identification information regarding associated individuals (e.g., names, addresses, Social Security numbers, etc.) may be protected by a less security-hardened system than genomic data 104-108 that includes such associations. In certain embodiments, the one or more data storage and/or processing systems 110-114 may include one or more secure, protected, and/or sandboxed execution environments for use in connection with the disclosed systems and methods, as discussed in more detail below.

In certain embodiments, prior to interacting with data managed by the one or more data storage and/or processing systems 110-114, the client system 100 and/or a user thereof may authenticate its identity and/or rights to interact with and/or otherwise use the data 104-108. For example, username and/or password authentication, biometric authentication, personal identification number authentication, and/or any other suitable type or combination of user authentication may be used in connection with authentication of the rights of the client system 100 and/or a user thereof to interact with and/or use data 104-108 and/or system 110-114.

The one or more data storage and/or processing systems 110-114 and/or the client system 100 may be configured to enforce privacy and/or policies associated with data 104-108 specified by stakeholders of the data (e.g., associated individuals, institutions that gathered the data, governmental authorities responsible for enforcing certain jurisdictional restrictions on the access or distribution of the data, etc.). The policies may articulate certain restrictions, conditions, requirements, and/or other actions associated with the access, use, distribution, and/or the like of the data 104-108. Such policies may be enforced in connection with interaction with, use, distribution, and/or the like of the data 104-108. For example, a policy may articulate that data 104-108 may only be used in certain ways and/or to derive certain computational results therefrom.

Examples of policies may include, without limitation, policies preventing and/or otherwise restricting interaction with, access to, use of, and/or distribution of data 104-108, policies articulating that certain security requirements be met prior to access, use, and/or distribution of data 104-108, policies articulating that certain actions be performed in connection with the access, use, and/or distribution of data 104-108 (e.g., anonymization activities, transformation activities, auditing activities, etc.), and/or the like. A variety of other types of policies may be associated with data 104-108, and it will be appreciated that any suitable type of policy, articulating restrictions, conditions, requirements, and/or actions to be enforced in connection with the interaction with, access to, use of, and/or distribution of data 104-108 may be used in connection with the disclosed embodiments.

It will be appreciated that a number of variations can be made to the architecture and relationships presented in connection with FIG. 1 within the scope of the inventive body of work. For example, without limitation, in some embodiments some or all of the functions performed by the client system 100 may be performed by the one or more genomic data storage and/or processing systems 110-114. Similarly, some or all of the functions performed by the one or more data storage and/or processing systems 110-114 may be performed by the client system 100. Thus it will be appreciated that FIG. 1 is provided for purposes of illustration and explanation, and not limitation.

Data Service Overview

In some collaborative models, research using genomic data may be conducted across distributed data centers by international teams of researchers operating on large, pooled genomic data sets. Such models, however, may introduce certain legal, ethical, and/or privacy considerations. Clinical settings where genomic data is used may also introduce a variety of potential storage and/or computing considerations to ensure trust and security of genomic information (e.g., cloud-based and/or hybrid storage considerations, data distribution considerations, security considerations, etc.).

Certain features that may work well in a local environment may not work as well in connection with a decentralized, distributed, and/or interconnected storage and computing network consistent with the disclosed embodiments. For example, in a single local environment, policy may be enforced through physical processes, including, for example, locking doors to prevent access to computing equipment storing sensitive data, using passwords to protect access to sensitive data, and/or the like. As described in more detail here, in a distributed architecture spanning multiple institutions, however, other, or additional, security and/or policy enforcement mechanisms may be needed to ensure that sensitive data and associated computing resources are used according to policies set by, for example, researchers, institutions, funders, patients, and/or participants providing the data. In certain embodiments, a data service is disclosed that may be associated with a distributed network that respects the policies of various stakeholders of genomic or other sensitive data.

Trust Management

Certain embodiments of the disclosed systems and methods may implement and/or otherwise include a trust management system that may allow governing authorities to assert that entities handling sensitive data meet certain baseline requirements for membership in an associated distributed network. These requirements may dictate, for example, that a participating entity demonstrate the physical security of a data center associated with the entity, that a certain level of data access and usage auditing is performed, and/or the like. If a would-be participating entity meets associated requirements, a trust management system may generate one or more cryptographic credentials that the entity may use to prove its identity to other participating entities and/or systems and to demonstrate compliance with associated network participation requirements. In further embodiments, such credentials may be used in connection with authenticating a user's identity and/or associated rights to access and/or otherwise use sensitive data. Consistent with embodiments disclosed herein, trust management may extend to many types of actors, entities, and/or institutions in associated distributed networks, including human actors, associated systems, and bioinformatic programs, thereby providing a framework that allows participants in one location to be trusted in others.

Policy Management

In a distributed system consistent with embodiments disclosed herein, various participating entities and/or institutions may be associated with different policies regarding data access and sharing, use of associated computing resources, and/or the like. In some embodiments, these policies may be articulated, encoded and exchanged between entities and/or institutions to ensure that the policies are respected and/or enforced, even on remote systems. For example, if a research study participant has consented to the use of his or her genomic data by a specific participating institution and/or in connection with a specific research study but not to broader uses of this data, a policy that expresses such conditions may be persistently associated with the participant's genomic data. In some embodiments, this policy may be enforced across the distributed network.

A variety of entities may inject policy into such a distributed network including, for example, researchers, research funders and/or institutions, pharmaceutical companies, governments, and/or the like. In some embodiments, the rights management and policy enforcement technologies described in the '216 patent and/or the '387 patent can be used to express and enforce such policies, although it will be appreciated that any suitable policy enforcement technology could be used.

Auditing

In certain embodiments, the disclosed systems and methods may enable data stakeholders in a distributed system—from individuals to institutions—to be able to view who has access to their data, what queries have been executed on their data, and/or the like. In further embodiments, developers of genomic and/or bioinformatics tools and/or applications may be able to view where and by whom their various tools and/or applications have been deployed and/or used. In some embodiments, a combination of a priori and a posteriori mechanisms may be implemented in connection with the disclosed systems and methods to ensure that sensitive data is transferred only under authorized conditions and/or to authorized destinations.

While trust and policy management tools may act on sensitive data before it is accessed, embodiments of the disclosed systems and methods implementing auditing mechanisms may allow for forensic investigation of data leaks after they have occurred. Auditing mechanisms may further provide support for liability analysis in connection with privacy-protection laws and/or regulations such as, for example, the Health Insurance Portability and Accountability Act ("HIPPA"), the Health Information Technology for Economic and Clinical Health Act ("HITECH"), or the like.

Encryption and Key Management

Once sensitive data has been released in the clear, it may be difficult to enforce data management policies and/or audit the use of this data. In certain embodiments, to ensure that data access is governed and auditable, sensitive data may be protected through encryption. In further embodiments, access to the keys that protect sensitive data may be governed, as access to these keys may allow for access to the sensitive data itself.

Secure Software

Embodiments of the disclosed systems and methods may provide certain assurances to researchers and/or other individuals or institutions that rely upon results of programs interacting with sensitive data over a distributed network. These assurances may include, for example and without limitation, some or all of the following:

That an application the researcher has specified for use in connection with genomic data is indeed the application that produced a returned result.

That other software on an associated remote system did not modify input or output data in a way that may change and/or compromise the results of the requested application's computation and/or other use of the sensitive data.

That keying material and/or secrets contained in the requested application were not leaked and/or otherwise distributed in the clear in connection with the use of the application.

In further embodiments, the disclosed systems and methods may provide for verification that a software module interacting with sensitive data originates from a trusted source, assurance that such a software module does not reveal sensitive data it should not (e.g., by uploading it to a third-party site or the like), and/or limiting the access by certain software modules from certain sources to certain computational resources and/or data.

Figure 2:
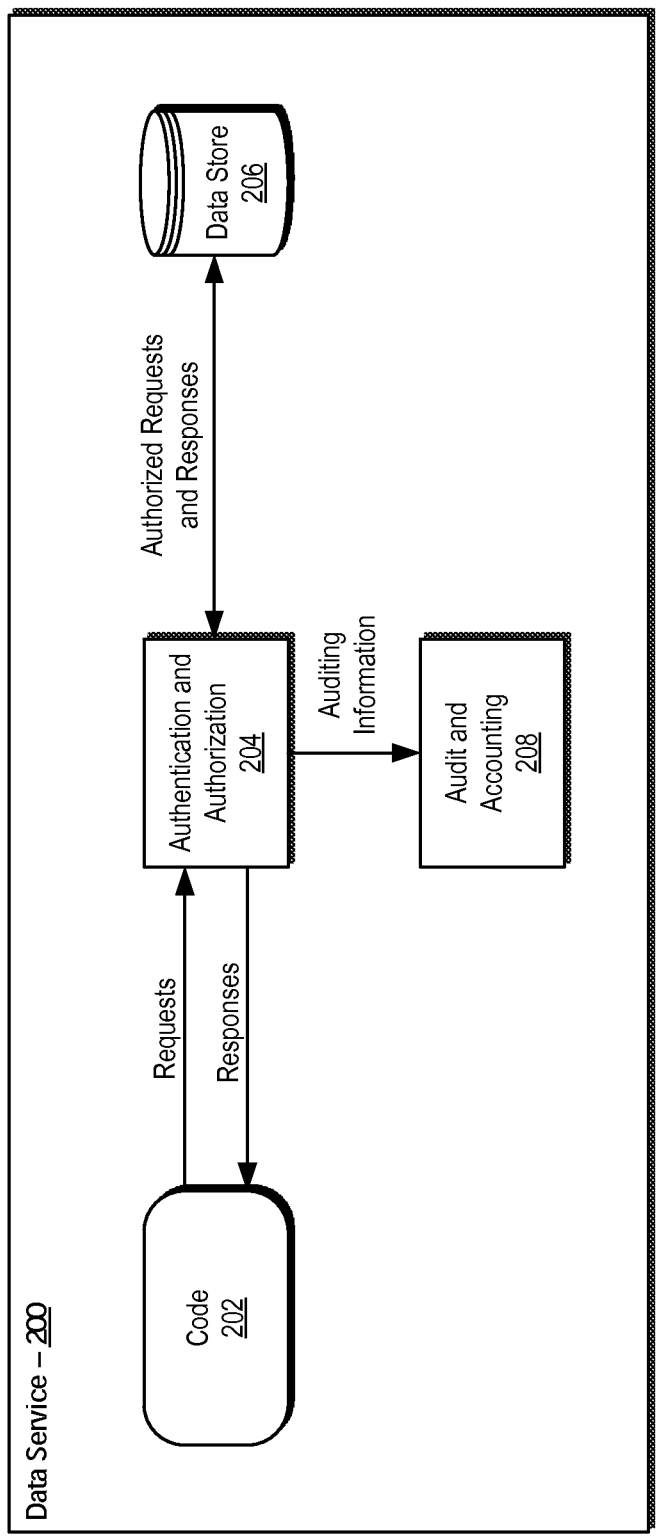
FIG. 2 illustrates an exemplary architecture for interacting with sensitive data using application programming interfaces consistent with embodiments of the present disclosure.

Rather than providing externally supplied software modules with direct access to sensitive data, certain embodiments of the disclosed systems and methods make use of application programming interfaces ("APIs"). FIG. 2 illustrates an exemplary architecture for interacting with sensitive data using APIs consistent with embodiments of the present disclosure. In certain embodiments, the illustrated architecture may be implemented in connection with a data service 200 (e.g., a genomic data service executing on a genomic data storage and/or processing system or the like).

As illustrated, one or more applications 202 may be loaded into the data service 200 by a user. In certain embodiments, the user may use a distributed client system communicatively coupled with the data service 200 in connection with their interactions with the data service 200. The application 202 may be configured to interact with data stored on a data store 206. For example, a researcher may create an application 202 used to issue requests to analyze genomic data managed by the data store 206 in connection with their research activities, and load the created application 202 into the data service 200. Among other things, the application 202 may be configured to issue one or more requests for certain genomic data managed by the data store 206 and/or computations to be performed in connection with the same and/or receive one or more responses to such requests. Although illustrated as local to the data service 200, it will be appreciated that in other embodiments, the data store 206 may be distributed.

From the perspective of the data service 200, the application 202 may be considered untrusted code. Accordingly, requests by the application 202 for access to data managed by the data store 206 may be routed through an API associated with an authentication and authorization module 204 of the data service 200. Information-revealing computations using the requested sensitive data may be performed in a secure environment behind the API, outside the direct access of the application 202. The authentication and authorization module 204 may authenticate a requesting principal's identity and/or an identity of the requesting application 202 (e.g., by examining a credential associated with the request or the like) and/or determine whether the requesting principal and/or application 202 is authorized to access and/or otherwise use the requested data (e.g., by enforcing an applicable policy and/or the like).

If a requesting principal and/or application 202 is authenticated and the associated request is authorized, the authentication and authorization module 204 may forward the authorized request to the data store 206. In response, the data store 206 may return a response to the authentication and authorization module 204 (e.g., a result from a requested computation and/or the like), which may in turn forward the response from the data store 206 to the requesting application 202. In certain embodiments, the response may comprise results of a computation and/or a process performed on requested genomic data managed by the data store 206. In further embodiments, the response may comprise genomic data and/or a subset thereof accessed from the data store 206. In some embodiments, information relating to the authentication and/or request authorization process described above may be sent to an auditing and/or accounting module 208 of the data service 200 and/or another service.

In some embodiments, the architecture illustrated in connection with FIG. 2 may use defined interfaces that may, for example, comprise Representational State Transfer ("REST") APIs. Among other things, the illustrated architecture may facilitate one or more of the following:

Discriminating amongst different principals and application of different policies to associated access requests through authentication of principals that wish to access sensitive data.

Granular access requests. For example, a principal and/or an associated requesting application can request only that subset of data that is required for a particular task.

Generation of audited access information so that if sensitive information is subsequently publicly disseminated, the potential source of the leaks may be more readily identified.

In certain circumstances, the illustrated architecture may allow sensitive data to be returned into an untrusted environment of application 202. For example, a request issued by the application 202 may comprise a request to determine a number of genomes that have a particular variant given a list of genome identifiers. A response from the API to such a request may comprise associated variants by RSID. Under such circumstances, the application 202 may be capable of learning individual variants for each of the genomes in the list included in the request, which may be chosen based on some other phenotypical characteristics. The secrecy of such associations may thus be compromised.

This potential concern may be reduced through use of a more sophisticated API capable of returning statistical information relating to a data set to a requesting application 202 without revealing individual variants, effectively moving information-revealing computations into a secured environment behind the API.

Data Access Proxy

The use of Application Programming Interfaces (APIs) may provide greater protection of sensitive data than direct access models, particularly when computations that may reveal information are performed behind the API and/or otherwise outside the reach of untrusted client-side code. However, designing an API that obscures all such computations may be difficult, as untrusted code may have undesirable access to intermediate computational results and/or products, potentially revealing more sensitive data than may be necessary and/or desired. Consistent with embodiments disclosed herein, general-purpose computational capability may be created within a trusted boundary of a genomic data service, thereby reducing the potential for revealing sensitive data.

Figure 3:
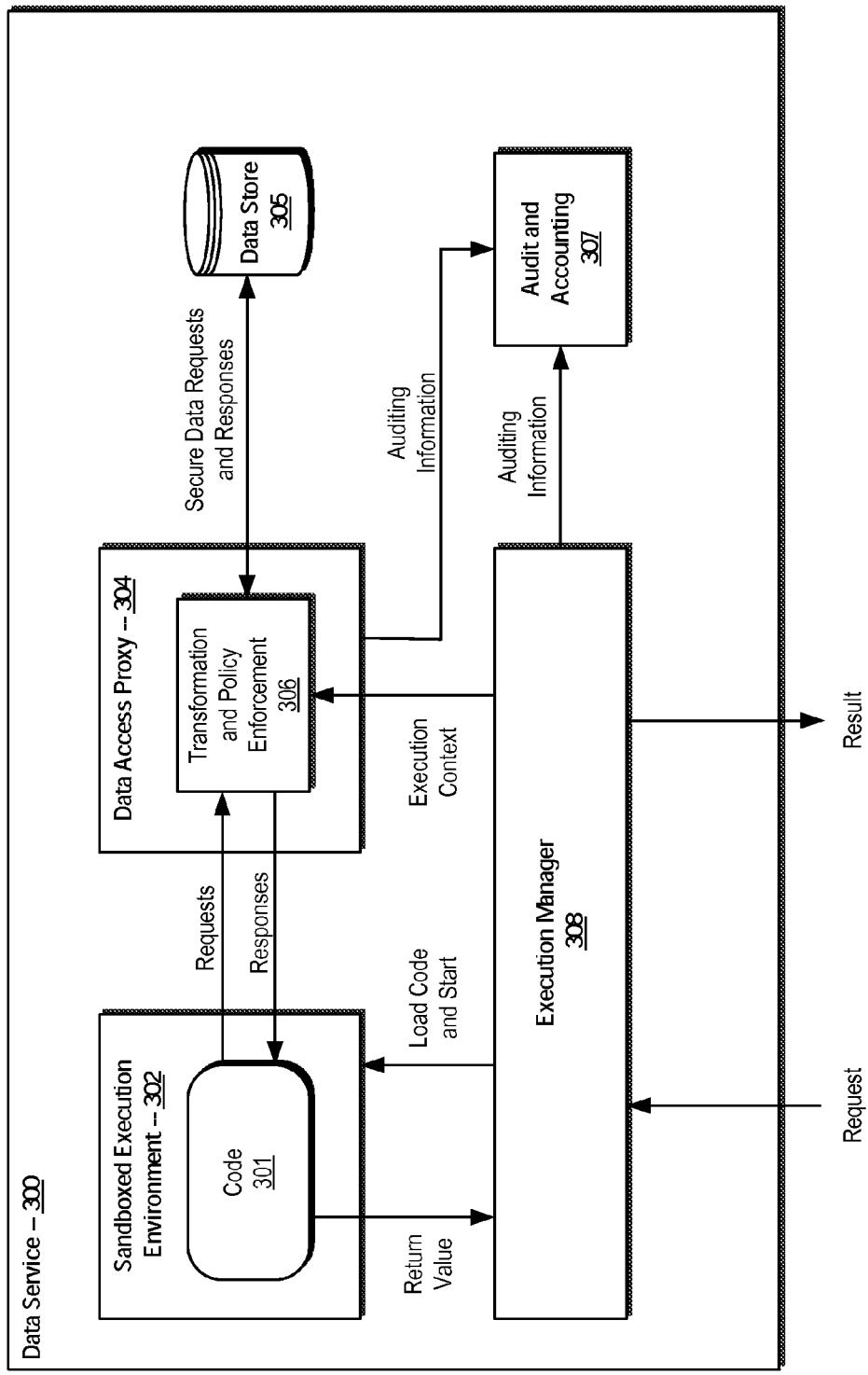
FIG. 3 illustrates an exemplary architecture for interacting with sensitive data using a sandboxed execution environment and a data access proxy consistent with embodiments of the present disclosure.

FIG. 3 illustrates an exemplary architecture for interacting with sensitive data using a sandboxed execution environment 302 and a data access proxy 304 consistent with embodiments of the present disclosure. In certain embodiments, the illustrated architecture may be implemented in connection with a data service 300 (e.g., a genomic data service executing on a genomic data storage and/or processing system or the like). Among other things, the illustrated architecture may move computations performed in connection with sensitive data managed by a trusted data store 305 into a trusted environment that allows for more precise control over information disclosed to (potentially untrusted) code and/or applications 301, which may be executed in a sandboxed and/or virtualized execution environment 302. In certain embodiments, information included in a final result of a computation may be provided to application 301, while intermediate results of associated computations may be exposed within the trusted boundary, but may not be exposed outside the trusted boundary (e.g., within the sandboxed execution environment 302).

In some embodiments, the illustrated data service 300 may implement a variety of features and/or functions to mitigate security and/or privacy threats associated with undesirable access to sensitive data, including, for example and without limitation, some or all of the following:

Code 301 may be examined to ensure that it is signed by competent and/or otherwise trusted authorities. In such instances, a successful signature check may be a condition for loading and/or executing code 301.

Signatures associated with code (e.g., potentially untrusted, third party, and/or externally supplied code 301) may enable auditing activities that may identify precisely which code accessed and/or otherwise interacted with sensitive data.

Code 301 may execute within a sandboxed execution environment 302 that may prevent it from accessing arbitrary computing resources, storage and/or network locations, and/or untrusted or unprotected execution environments.

Code 301 may be required to interact with and/or otherwise access data through a granular API, thereby improving auditability of such interactions and reducing the amount of sensitive information that may be compromised in connection with computations performed using that (or related) data.

In certain embodiments, programs (e.g., code 301) may be developed for use in connection with the data service 300 in an untrusted environment (e.g., a user's client system). The programs may be tested by developers using public data (e.g., over unsecured HTTP or the like) to verify that the developed programs and/or applications operate as desired. Once a program is verified, it may be uploaded to the data service 300. In some embodiments, uploading the program to the data service 300 may further include verifying that the developer is authenticated (e.g., possesses credentials issued by a trusted authority and/or the like) and/or allowing the developer to set certain policies governing the use of the uploaded program. Various assertions about the program including, for example, digital signatures asserting certain properties associated with the program, may be added at upload and/or at a later time.

To provide a certain degree of isolation and/or security, in some embodiments programs uploaded to the data service 300 may be executed in virtualization containers and/or in a sandboxed execution environment 302 (e.g., a limited virtualized execution environment and/or machine). Programs and/or software code executing in a sandboxed execution environment 302 may be restricted to a controlled set of resources, functions, and/or services associated with the data service 300. For example, a sandboxed execution environment 302 may allow software code executing therein to access only a certain subset of data sources governed by data service 300. Access to certain input/output channels, APIs, networking resources, processing resources, temporary storage, and/or the like may be similarly controlled and/or restricted.

Virtualization and/or sandboxing can be implemented in any suitable manner. In some illustrative embodiments, virtualization may be implemented using Docker™ (e.g., a system based on a Linux container mechanism ("LXC")). When user-developed programs are loaded into the data service 300, the system may create executable images of the programs and save them to a repository for retrieval at execution time. In some embodiments, such executable images may be created automatically in response to a program being loaded into the data service 300.

As illustrated in FIG. 3, a request to execute a particular program, such as, for example, code 301, may be received by the data service 300 from a user's system. In certain embodiments, the request may be issued from a client system that may be remote and/or otherwise distributed from the system associated with the data service 300. In some embodiments, the request may be passed through an authentication and/or authorization process to ensure that the principal requesting the execution of a given computation is allowed by policy to do so.

The request may be received by an execution manager component 308 of the data service 300. Among other things, the execution manager 308 may be configured to manage the lifecycle of a computation running on the data service 300, manage interactions between users and the data service 300, and/or engage in auditing and accounting activities relating to the use of the data service 300. For example, the execution manager 308 may be configured to receive requests from a client system, send associated responses to the client system, and/or interact with the sandboxed execution environment 302 and/or code 301 executing therein, a data access proxy 304, and/or an audit and/or accounting module 307 in connection with embodiments of the disclosed systems and methods.

In response to receiving the request, the execution manager 308 may load the requested program 301 into the sandboxed execution environment 302. In some embodiments, the execution manager 308 may further perform a policy identification and/or enforcement process and, in response thereto, place one or more conditions on the requested program 301. For example, prior to executing the requested program 301, the execution manager 308 may require verification that the requested program 301 be digitally-signed by a trusted authority.

An execution context may be generated by the execution manager 308 for the requested execution of the program 301. In some embodiments, the execution context may allow the data service 300 to associate sensitive information (e.g., genomic data managed by data store 305) with an executing program 301 without placing the sensitive information into the address space of the program 301 where it may be vulnerable (e.g., within the sandboxed execution environment 302).

As an example, the exemplary program 400 illustrated in FIG. 4 may be passed a genomic ID as its first argument. In some embodiments, the program 400 may check for variants in particular exons of the PIK3CA and PTEN genes. A malicious or erroneous program may reveal this genomic ID, which, under some threat models, may allow attackers to piece together private and/or otherwise sensitive information. To mitigate this threat, the program 400 may be handed an ephemeral identifier to use for the duration of its execution. In some embodiments, this identifier may be a random identifier. In further embodiments, the identifier may comprise a result of applying a relatively difficult-to-invert function (e.g., encryption functions, hashing functions, etc.) to the actual identifier. In some embodiments, the mapping between actual identifiers and ephemeral identifiers may be maintained as part of the execution context generated by the execution manager 308.

In further embodiments, the execution context generated by the execution manager 308 may comprise information used to anonymize data and/or responses from the data store 305. For example, in some embodiments, the execution context may comprise information used to introduce noise to data and/or responses from the data 305 designed to anonymize the returned data and/or responses. For example, techniques such as those described in the '624 application could be used.

Referring back to FIG. 3, the execution manager 308 may initialize a virtual machine instance (e.g. a virtualized and/or sandboxed execution environment 302) and start the requested program 301. The execution manager 308 may further pass any necessary execution parameters to the program 301 within the virtualized execution environment 302. In certain embodiments, the parameters may be passed to the program 301 in a transformed state to avoid allowing the program 301 access to sensitive information.

As the program 301 executes, it may request data from the data store 305. In certain embodiments, these requests may comprise HTTP calls, as shown in connection with the exemplary program 400 illustrated in FIG. 4. Because the program 301 may execute within a virtualized execution environment 302, the ability of the program 301 to access certain resources (e.g., network resources and/or endpoints) outside a designated set of resources may be restricted.

In some embodiments, requests for data from the program 301 may be routed through a data access proxy 304 of the data service 300. Among other things, the data access proxy 304 may transform requests and/or responses received from and/or sent to the program 301 executing in the virtualized execution environment 302 to protect the integrity of sensitive information managed by the data store 305. In certain embodiments, the data access proxy 304 may be transparent to the program 301. For example, from the perspective of the program 301, the program 301 may initiate requests and receive responses as if it were communicating directly with the data store 305.

In some embodiments, the data access proxy 304 may comprise a transformation and policy enforcement module 306. The transformation and policy enforcement module 306 may transform requests received from the program 301 into secure data requests, transform responses received from the data store 305 prior to returning the responses to the program 301, enforce applicable policy relating to the interaction of the program 301 with the data store 305, and/or the like. In certain embodiments, the transformation and policy enforcement module 306 may use the execution context provided by the execution manager 308 in connection with its various activities. For example, in some embodiments, the execution context may comprise information used to effectuate transformation and/or policy enforcement actions performed by the transformation and policy enforcement module 306.

In some embodiments, the transformation and policy enforcement module 306 may prohibit or modify access to information in data store 305 based on relationships between the originators of data stored in data store 305, the principal on whose behalf program 301 is being executed, the creator of program 301, and/or the like. For example, if a particular datum in data store 305 concerns a specific individual who has established a policy preventing access to a specific subset of genomic information by all principals except for her physician, the transformation and policy enforcement module 306 may determine that the program 301 has requested access to the forbidden information, but is not being executed on behalf of the individual's physician, and thus may prevent access to this data.

In some embodiments, functions performed by the data access proxy 304 and/or the transformation and/or policy enforcement module 306 in connection with request and/or response transformation and/or policy enforcement activities may include, without limitation, some or all of the following:

- Requests may be transformed using information included in the execution context provided by the execution manager 308. For example, the transformation and/or policy enforcement module 304 may determine how ephemeral identifiers given to a program as parameters map to actual identifiers in the data store 305. In some embodiments, the execution context provided by the execution manager 308 may be further provided to the data store 305 by the transformation and/or policy enforcement module 304 in connection with secure requests.
- A request from the program 301 having a first level of security may be increased to a second, higher level of security prior to transmission to the data store 305. For example, a request made over HTTP may be transformed to a secure HTTPS request with certificates at both the client and server. In certain embodiments, this may ensure that only legitimate, certified systems directly interact with the data store 305.
- Policies may be applied and/or otherwise enforced in connection with authorizing a request issued by the program 301. In some embodiments, policies may offer granular control over access to sensitive data as they may be applied as a computation proceeds rather than just before a computation begins. For example, in certain embodiments, enforced policies may be responsive to a manner in which a computation proceeds, even if the set of requests that a program will make may not be determined in advance.
- A destination of a request may be rewritten. For example, if a request can be satisfied by a number of different servers and/or data stores 305, the data access proxy 304 may direct the request to the closest, or otherwise more suitable, servers and/or data stores 305.
- A request and/or an associated response may be logged for auditing purposes.

Results from the data store 305 generated in response to a secure request may be received by the data access proxy 304 and/or the transformation and/or policy enforcement module 306. In certain embodiments, upon receipt of the response, the data access proxy 304 and/or the transformation and/or policy enforcement module 306 may enforce associated policy and/or transform the response prior to returning the response to the program 301 executing in the virtualized execution environment 302 (e.g., returning the response to the address space of the program 301). In some embodiments, this policy enforcement and/or transformation may be based, at least in part, on information included in the execution context generated by the execution manager 308.

In some embodiments, the transformation and/or policy enforcement module 306 may transform results returned from data store 305 to manage the amount of sensitive information returned into the address space of program 301. Such transformations may include, for example, eliminating certain fields in the response from data store 305, changing or adding randomness to certain values in that response, reducing the precision of values in the response, or returning an error to program 301 instead of a valid response.

Upon termination of the program 301, its output, a transformed version thereof, and/or a return value may be captured by the execution manager 308 and may be returned to an original requestor (e.g., a user and/or a distributed client system interfacing with the data service 300). In further embodiments, auditing information relating to interactions between and/or operations of various elements of the data service 300 may be provided to an auditing and/or accounting module 307 of the service 300. In certain embodiments, auditing information may be digitally-signed so that its authenticity may be verified later. In yet further embodiments, because the data service 300 may use virtualization on known virtual machines, and may store, sign, and/or tag various state information associated with its operation, computations may be recreated at a later time to validate various auditing information (e.g., recreated on a different system at a later time or the like).

In some embodiments, some programs 301 may comprise continuous computations that do not terminate after computing a single result. Such computations may, for example, collect information as it comes into the system, and return outputs to execution manager 308 according to the newly assimilated data. For instance, a program 301 may be monitoring a data store 305 for a cancer diagnosis. Upon a new diagnosis, the computation may look up the genetic information for the patient in a second data store and refine a model for genetic prediction of cancer. As new diagnoses enter into the data store, the cycle repeats and the model is refined further.

In some embodiments, some programs 301 may, in the natural course of computation, or under the control of the execution manager 308, be suspended and wait for some event, or travel to another data service 300 in order to do computations under a different set of policies or over a different set of data. For instance, a program that compares the APOE status in mainland Chinese populations with Icelandic populations, may travel multiple times between data services located in China and data services located in Iceland in order to comply with local policy and/or to access different data stores.

In some embodiments, some parts of a program 301 may be involved in determining an optimal data service 300 location for a particular purpose. For instance, a program 301 may consider the number of data points available in a data store 305 versus their accuracy. For example, a program modeling progression of childhood mitochondrial disease may decide to move to a location where the data are less accurate but far more numerous.

Data Service API

As discussed above, in some embodiments of the disclosed systems and methods, requests by an application for access to sensitive data and/or for computations to be performed using such data may be routed through an API that may be defined semantically by an associated system. In certain embodiments, information-revealing computations using requested sensitive data may be performed in a secure environment behind the API outside the direct access of the untrusted application. Certain embodiments of the disclosed systems and methods may use REST APIs in connection with interactions with genomic data. FIG. 5 illustrates an exemplary exchange 500 between a service that exposes variant data via an API and a requesting program.

In some embodiments, the disclosed data service may be language agnostic, and associated programs for interacting with the sensitive data may interface with the data service via HTTP APIs. In certain embodiments, programs used to interact with sensitive data may handle user I/O using standard stdin, stdout, and stderr facilities. For example, as discussed above, the exemplary program 400 illustrated in FIG. 4 may check for variants in a given set of genes and exons. In some embodiments, the program 400 may receive an identifier of a genome record as its first command line argument and may write its results to stdout.

Governed Execution Example

Figure 10:
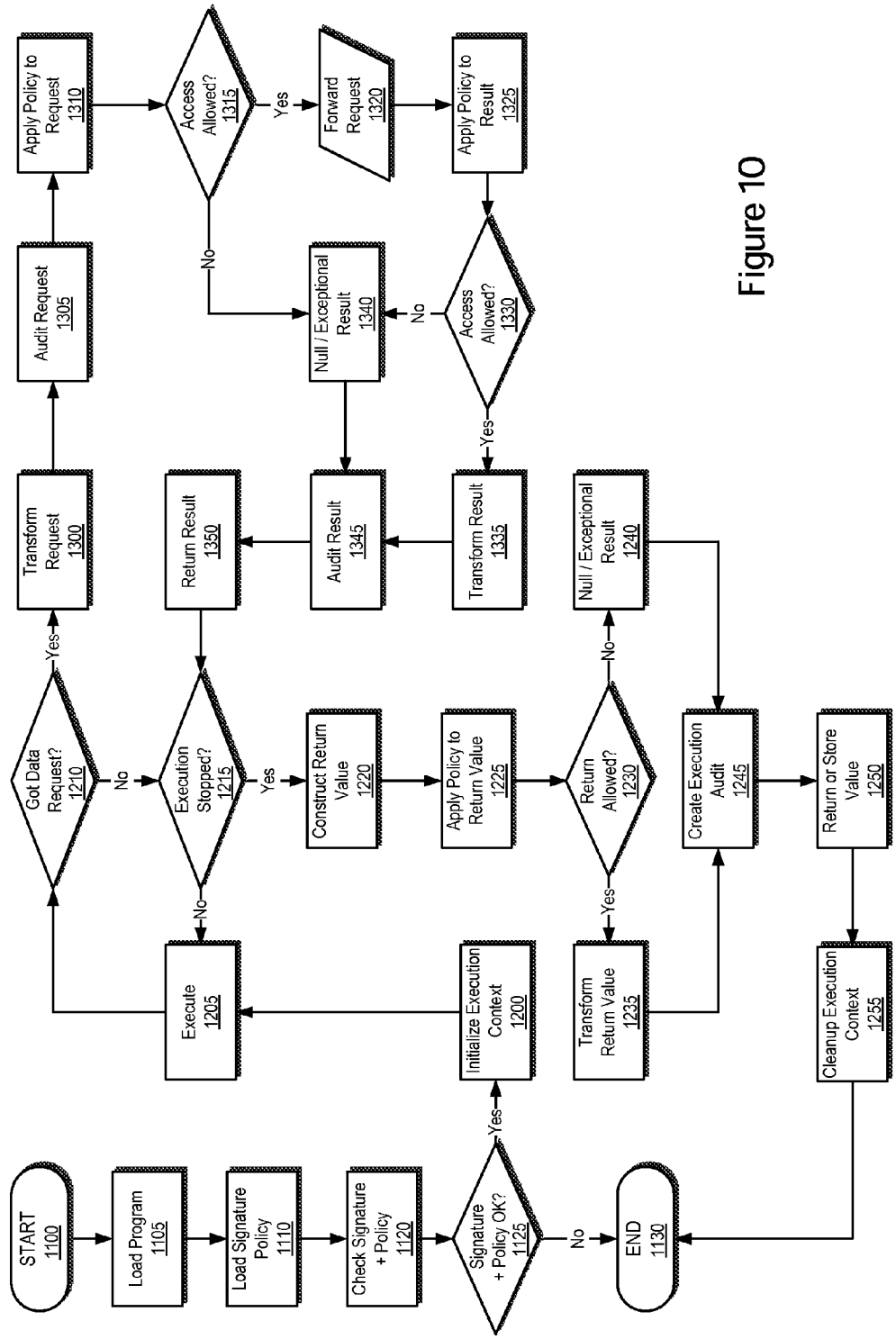
FIG. 10 is a flowchart illustrating the execution of a program or other computation by a data service in accordance with certain embodiments of the inventive body of work.

FIG. 10 is a flowchart illustrating the governed execution of a program or other computation (e.g., program 301) by a data service (e.g., data service 300) in accordance with certain embodiments of the inventive body of work. Referring to FIG. 10, at 1100 processing of the governed computation begins. At 1105, the program is loaded, e.g., from a program store, possibly external to the system executing the program. The program may take the form of a code bundle plus metadata, a virtual machine with the desired program pre-loaded, or any other packaging or encapsulation mechanism for a computation. At 1110 the policy that describes required authentication policies is loaded. For example, this might be a policy document stored in an external policy store, or it might be looked up in a database of policies associated with the principal requesting the execution, the data resources that are to be accessed, and so forth. At 1120 signatures—or other assertions—are evaluated against the policy loaded in the previous step. If the signatures or other assertions meet the policy requirements (i.e., a "yes" exit from block 1125), then execution proceeds. Otherwise, execution halts (1130).

Following a successful policy check at 1120/1125, the execution context is initialized at 1200. As described elsewhere herein, in some embodiments this may comprise creating or populating a data structure (e.g., the execution context) that will hold information about the computation. In some embodiments, the execution context may contain metadata about the computation being performed, including, e.g., mappings between ephemeral identifiers generated for resources and the true identifiers of those resources.

At 1205 the program begins to execute. This may involve starting a virtual machine or other execution container, running a script, executing a program on a byte code interpreter, and/or the like. The program is provided with the arguments it needs to run, information about where to fetch resources it needs, locations for output, and so forth.

Upon beginning execution of the computation, the execution environment listens for, and intercepts, requests for access to data (1210). By intercepting the requests coming from the governed computation, policy can be applied, results can be obscured, identifiers remapped, and so forth. Essentially, at this stage techniques are applied to ensure that the information being delivered to a computation is appropriate under some set of policies.

The request might be intercepted using one or more different techniques. One implementation might use a transparent proxy on the same subnet as a virtual machine or container executing the computation. The program executing inside the container believes that it is accessing a normal URL, but in fact, its request is intercepted and processed by a proxy server that performs steps both on the request and response, as shown at 1300-1350.

For example, if the secure execution context received a request for data, it first applies any appropriate transformations to the request, possibly using information in the execution context to do so. For example, in some implementations, programs may request access to resources using a REST API. A program might ask for a specific genomic variant like this:

http://geneserver.genecloud.com/genome/123/variant/rs93458

The URI might be transformed, using information in the execution context, to substitute in the true identifier for this genome. For example, the URI may become this:

http://geneserver.genecloud.com/genome/98482842872348/variant/rs93458

Where the mapping between the ephemeral identifier "123" and the true identifier "98482842872348" is part of the execution context.

It will be appreciated that other transformations are possible; for example, mapping resource specifiers in one namespace to another namespace. Many online resources use their own unique names for genes; these names might be mapped to more standardized names.

As a further example, rather than substituting in a true identifier for an ephemeral identifier, the system might use a hashed or encrypted version of the true identifier as arguments for the execution of the program, and this transformation step may involve adding an HTTP header to the request that allows the destination server to determine the true identifier.

In some embodiments, the destination of the request may also be changed, to reflect knowledge of the regulatory landscape, the most convenient copy of the data, the specific database known to contain the desired information, and/or the like.

As shown at 1305, in some embodiments requests are audited. The audit may contain the original request, the transformed request, a request obscured by encryption (e.g. to prevent information leakage to inappropriate parties via the audit), etc.

At 1310, policy is applied to the request. For example, policies governing resource access are applied to the request to determine whether specific accesses are allowed. In one embodiment, the policies are applied during the execution of the computation, not a priori. The benefit of this setup is that a computation may determine as part of its execution which resources are to be accessed, resources whose identifiers may not be known a priori so that authentication cannot be determined in advance.

For example, a program may request from a server a list of genomes matching a specific criterion, e.g. they have variant rs1234. A subsequent step might then interrogate the dynamically-determined cohort to investigate correlations between variants rs1234 and rs5678. The specific accesses requested in the second step of this computation are not known (and generally cannot be known, since they depend upon the state of the specific genomic database being queried) in advance. In such circumstances, the authorization of such requests should be done at runtime.

Referring once more to FIG. 10, at 1315 a determination is made as to whether the policies of the previous step allow the access. If access is allowed, the request is forwarded to another system that stores the governed information. For example, if the resources are identified via a REST API, as outlined at (1300), the request is forwarded to this system.

At 1325, policies, if any, are applied to the results of the computation. The results returned from a sensitive data sources may, for example, themselves be subject to governance policies that cannot be evaluated before the result is generated. For example, a very specific query that narrows down a cohort to a single person, in a way that may render that individual subject to identification, may be blocked.

At 1330, a determination is made as to whether to allow access to the results, and at 1335 the results may be transformed, if dictated by policy. Transformations may be applied on the returned values for several reasons, including (a) inverting mappings made previously, e.g., at 1300, possibly using information in the execution context, (b) adding randomness to results that are determined to return too much personal information, etc.

If access is not allowed (e.g., a "no" exit from block 1315 or block 1330), then at 1340 a null/exceptional result is returned, signaling that an exceptional case has happened. This step should also be governed carefully, as sometimes returning an exception result may leak information as well—for example, showing that a given individual is not part of a database. At 1345, the result may be audited, like the request, in raw form, transformed form, or even encrypted or otherwise obscured form to prevent casual log viewers from seeing information they should not see. The system may also perform an "information accounting", determining and recording the amount of information about a specific resource that has been revealed. This may be used in future policy decisions; if too much information has been revealed according to some policy, the system may refuse to answer further questions.

At 1350, a result is returned back to the program under execution. For example, if the request was intercepted by a transparent proxy, in this step, the proxy provides the result back to the requester.

At 1215, a determination is made as to whether execution of the governed program has terminated. If not, the process continues execution at block 1205.

At 1220, a return value is constructed. For example, in one embodiment when the governed computation has terminated, the final result of this computational step is assembled into a data structure to be returned to the principal requesting the computation.

At 1225, policy is applied to the potential return value. In the same way that the results of each of the individual resource requests was governed and audited, so too, in some embodiments, are the combination of these results. Otherwise, a program could make a very long series of seemingly innocuous queries and combine the results together into something that reveals a great deal of information. The types of policies applied may, for example, be similar to those described in connection with block 1325, but they tend to concern combinations of information. For example, a policy may require that "incidental findings" are either revealed or suppressed, depending on the severity of those incidental findings. This might mean, for example, that a detected variant indicating an increased chance for a specific disease like Alzheimer's (for which there is currently no medically proven course of action to avoid the condition) be suppressed in a final result. This suppression may be the result of an institutional policy, or a personal preference of the principal from whom the data was collected.

At 1230, a determination is made as to whether return is allowed by the policy, and at 1235 the return value may be transformed, similar to block 1335, but for the final results. For example, each of the return values may be modified slightly to maintain confidentiality, while preserving the statistics (e.g. mean, variance) of the results.

If access is not allowed, then a null/exceptional result may be returned, similar to block 1340, and at 1245, an execution audit may be created. The final result may be audited, of course, but in some embodiments some or all of the inputs and the entire state of the system as a result of this computation are audited as well. This step may be desirable for forensic purposes, to recreate results that were obtained in the past. Suppose, for example, that a computation is used to dose a medication and the patient suffers an adverse reaction. It is important to know that the computation was performed correctly, and to be able to demonstrate this fact. One method for doing this involves computing and storing hashes on the inputs and all implicit input state, the computations themselves, and the output results, possibly in a digitally signed form. By storing the hashes along with the input and output data, state data, and results, a very large class of computations (e.g., those that are deterministic and referentially transparent) can be recreated exactly.

At 1250, the results are returned to the requester, or stored in a well-defined location for later processing stages, and at 1255 the execution context is cleaned up. For example, the execution context that contained metadata about this computation may be destroyed, after which processing stops.

It will be appreciated that FIG. 10 has been provided for purposes of illustration, and not limitation, and that a number of changes could be made to the example process shown in FIG. 10 without departing from the principles of the inventive body of work. For example, in some embodiments, various blocks could be omitted, other blocks could be added, steps could be performed in different order, and/or the like.

Some examples of additional details of, and possible variations to, the example process described above are provided below.

Identifying Resources to the Computation

One of the reasons that some embodiments virtualize computations is based on the security assumption that any information given to the computation itself may potentially be leaked, whether accidentally or maliciously. There are several mechanisms for protecting against this eventuality.

At block 1200 in FIG. 10, an execution context is created that may contain (among other things) mappings between identifiers known to the system and identifiers as given to the computation. In some embodiments, a computation is given a random, ephemeral alias for a resource in the context of this specific execution. For example, a resource that has an actual identity 12345678 may be assigned a random identifier 072963429. When the computation desires information about this resource, it asks for 072963429. The system, using the execution context, maps this identifier to the true identifier 12345678.

An additional approach is to encrypt true identifiers using a key known to (or discoverable by) the servers hosting the sensitive data. A variation would be to use a keyed hash function (such as HMAC) and to use the hash as the resource identifier. Those skilled in the art will appreciate that there are many potential ways to obscure the identifier, and that any suitable technique could be used.

One benefit of this approach is that it is compatible with testing computations against test data, with computations being run outside of the trusted execution context. In such cases, there is no execution context, no proxy, and hence no translation. If the tester knows some genome identifiers that have been made public, the computation may be tested outside of the trusted execution context and then subsequently uploaded to the trusted context.

Computational Networks

Consistent with the disclosed embodiments, computations that may potentially reveal sensitive information may be isolated and/or otherwise be performed in a virtualized and/or protected execution environment (e.g., in a sandboxed environment). In further embodiments, more complex computations may use multiple stages that may further be individually isolated in protected processing environments. In some embodiments, isolating stages of a computation may, among other things, improve security of the computation and/or reduce the potential for sensitive information and/or intermediate computation information from being undesirably revealed.

As an example, a computation may determine carrier compatibility. A program configured to implement the computation may identify two subjects by a phenotypic identifier, check the subjects for the presence or absence of a particular variant, and determine whether the two subjects are carriers. Such a computation may, however, potentially reveal personally-identifiable and/or otherwise sensitive information. To reduce this risk, consistent with certain embodiments disclosed herein, the program may be implemented using a network of three separate programs such that each, run in isolation, may not make the connection between genotype and phenotype.

Figure 6:
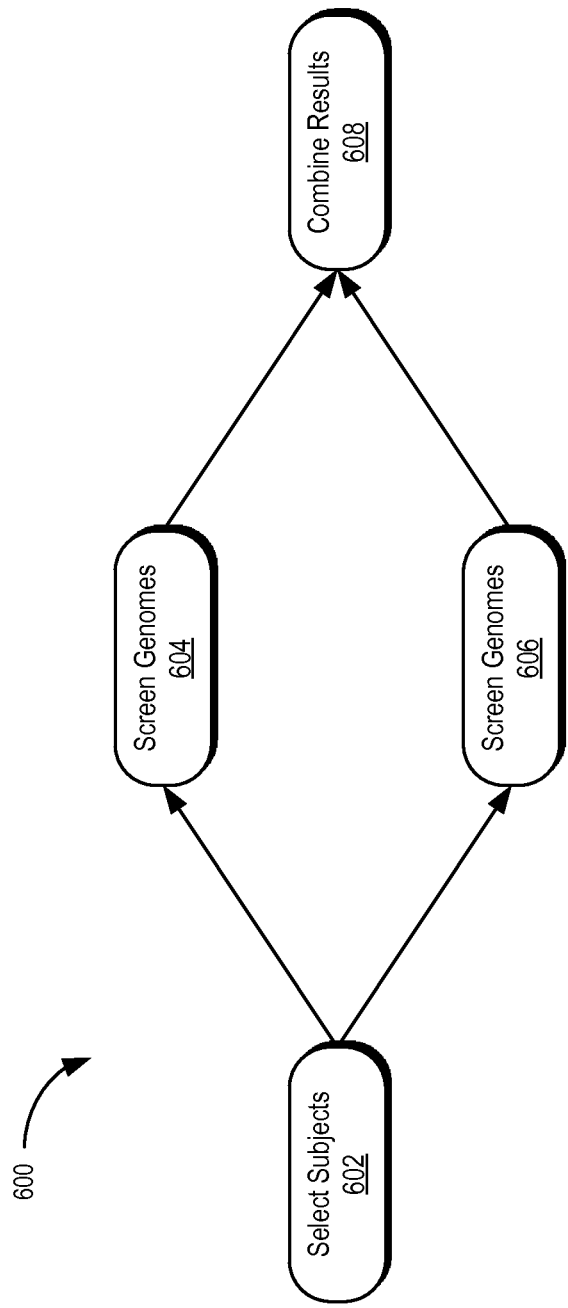
FIG. 6 illustrates an exemplary computational network for performing computations utilizing sensitive data consistent with embodiments disclosed herein.

FIG. 6 illustrates an exemplary computational network 600 for performing computations in connection with genomic data consistent. Particularly, the illustrated computational network 600 may implement the above-described computation for determining carrier compatibility. As shown, the computational network may separate different computations (e.g., computations 602-608) into isolated address spaces. For example, the select computation 602 may identify two subjects based on phenotypical criteria and/or any other suitable method. Identifiers associated with the selected subjects may be mapped into a genome identifier outside the address space of the program implementing the select computation 602. Each genome may then be assessed separately in screen computations 604, 606 to check for the presence of a particular variant. The screen computations 604, 606 may pass results to a combine computation 608 (e.g., Boolean values indicating whether the variant is present and/or is not present), that may determine carrier compatibility based on the results (e.g., by performing a logical AND or the like). Although the illustrated computational network 600 may otherwise be implemented using a single program, the amount of personally-identifiable and/or otherwise sensitive information that may possibly be revealed is reduced.

In some embodiments, each of the computations 602-608 may be performed inside of a sandboxed execution environment, as illustrated in FIG. 3, with the execution manager 308 governing the interactions between each of the individually sandboxed computations. For example, the computation 602, if running inside of a sandboxed execution environment 302, may return its results to the execution manager 308, which then provides those results, possibly after some transformation, to programs 604 and 606, each running inside of their own sandboxed execution environments.

Certain embodiments of the disclosed data service may provide various mechanisms for specifying computational networks including, for example, computational networks such as that illustrated in connection with FIG. 6. In certain embodiments, the disclosed data service may, among other thing, facilitate transformations between modules, computational lifecycle management, storage and/or transport of intermediate computational products, and/or returning final computational results in a secure manner.

Model/View/Controller Architecture

Figure 7A:
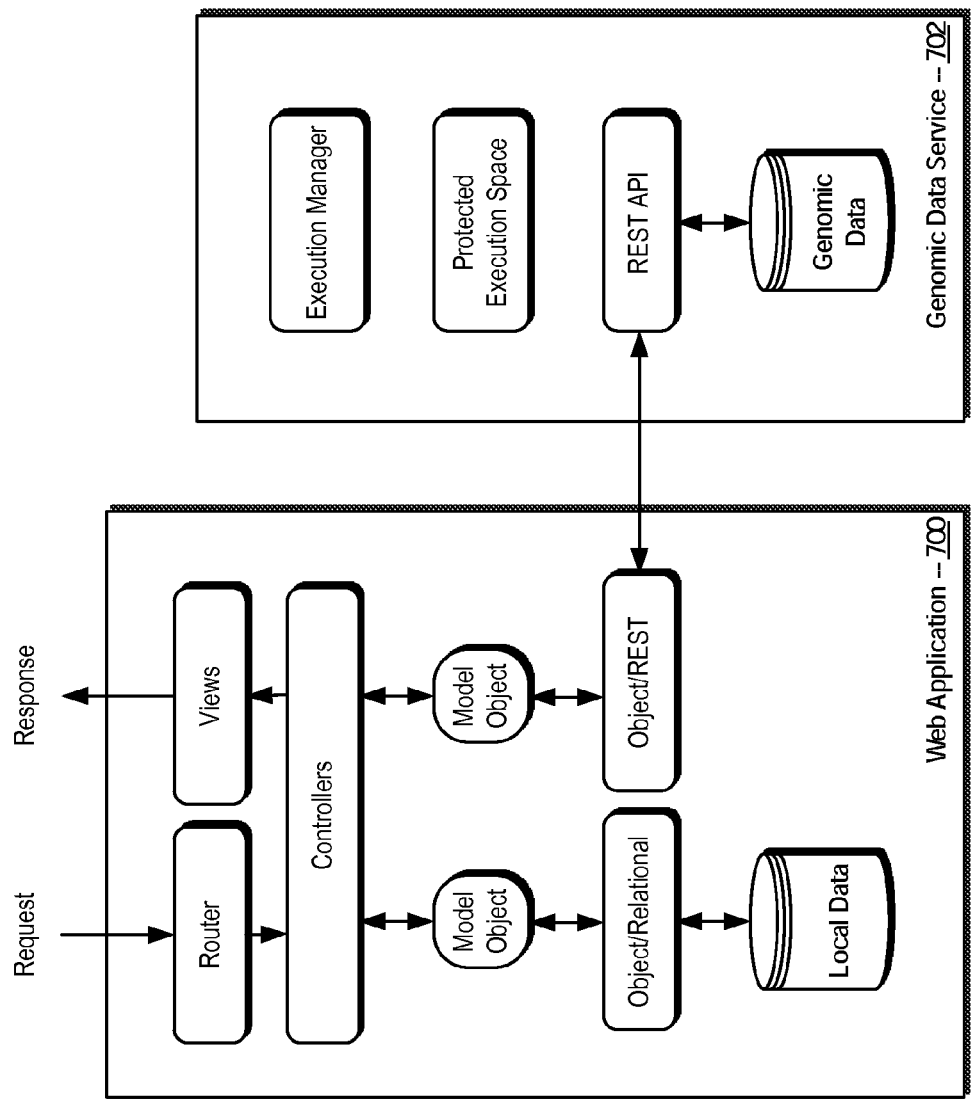
FIG. 7A illustrates an exemplary web application configured to interface with a data service consistent with embodiments disclosed herein.

In some embodiments, a Model/View/Controller web-application architecture may be implemented in connection with an embodiment of the disclosed data service framework. FIG. 7A illustrates an exemplary Model/View/Controller web application 700 configured to interface with a genomic data service 702 consistent with embodiments disclosed herein. In some embodiments, the genomic data service 702 may expose a secure API to facilitate interaction with genomic data managed thereon (e.g., a REST API).

In certain embodiments, an object-relational model ("ORM") implemented in connection with the web application 700 may be adapted to interact with the secure API. In some embodiments, an ORM system may be designed to allow application developers using web services frameworks such as Ruby on Rails or Django to interact with automatically-generated model objects whose class corresponds to a database table, and whose object instances correspond to rows within the table. In further embodiments, web frameworks may be used supporting components that allow developers to transparently interact with a model object stored in a remote service over a REST API in a similar manner as for an object in a local database.

As an example of Object/REST mapping, a statement that retrieves a database record may be translated into a URL. For example, a statement that retrieves the database record patient.rsid (1933437), may be translated into the URL http:// . . . /genome/5685c028bf7811e3a21a12470ec1d3b5/variant/rsid/rs1933437, where the genome ID is associated with the patient object in the local database and the path is constructed automatically by the object to a REST mapping layer. In some embodiments, such a request may be coupled with an authentication mechanism that allows code making the request to be identified and/or audited.

Certain embodiments of the disclosed systems and methods may be integrated at an API level in a variety of circumstances including, without limitation, when associated computational modules:

Originate from a trusted source that may not need to be authenticated during the transitions;
Have been analyzed for undesired behavior;
Do not necessarily need proof of integrity for access to sensitive data such as genomic data;
Are executed in a trusted environment that may ensure that the sensitive information being retrieved by the modules may not be compromised by other components; and/or
Can pass intermediate products between various computational modules safely and/or without otherwise compromising the integrity of the sensitive data.

Figure 7B:
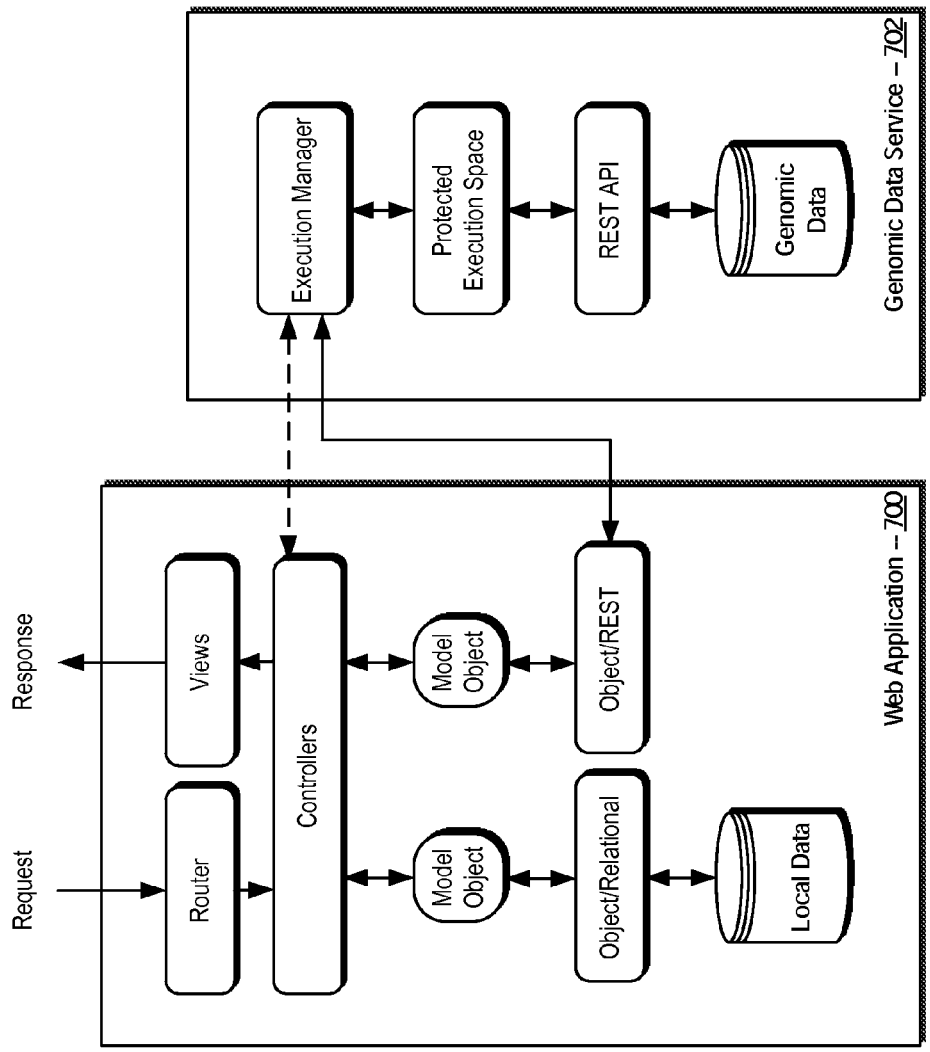
FIG. 7B illustrates an exemplary web application configured to interface with a data service using a data access proxy consistent with embodiments disclosed herein.

In further embodiments, such as when one or more of the above circumstances do not apply, certain protection may be achieved by applying sandboxing and/or virtualized execution environment techniques at an individual module level consistent with other embodiments of the disclosed systems and methods. FIG. 7B illustrates an exemplary web application 700 configured to interface with a genomic data service 702 using a protected execution environment.

In some embodiments, sandboxed modules may be invoked by controlled code directly. For example, modules themselves may use an Object/REST mapping as described above, with an adapter being injected as a dependency into the virtualization container. In certain embodiments, this approach may be implemented in circumstances where there may not be many dependencies on other module objects and/or where necessary parameters may be passed to the sandboxed modules as parameters.

In further embodiments, a level of indirection may be implemented. For example, rather than mapping instance variables and method access to REST calls that return those items, an object mapping may convert those requests into commands to execute the sandboxed modules, passing in any necessary parameters.

Utilizing module-level sandboxing may, among other things, allow the genomic data service 702 to more safely handle third-party code, cryptographically verify code integrity, and/or the like. In certain embodiments, to mitigate risk to intermediate products and/or computational information (e.g., that may be returned to a web-application in certain architectures), computational networks may be used in connection with the genomic data service 702 framework. Particularly, as discussed above, a computational network may be specified to isolate certain intermediate computations of a computation and/or program. Consistent with disclosed embodiments, various intermediate computations may be executed within various protected execution environments, thereby protecting the integrity of intermediate computational results.

Figure 8:
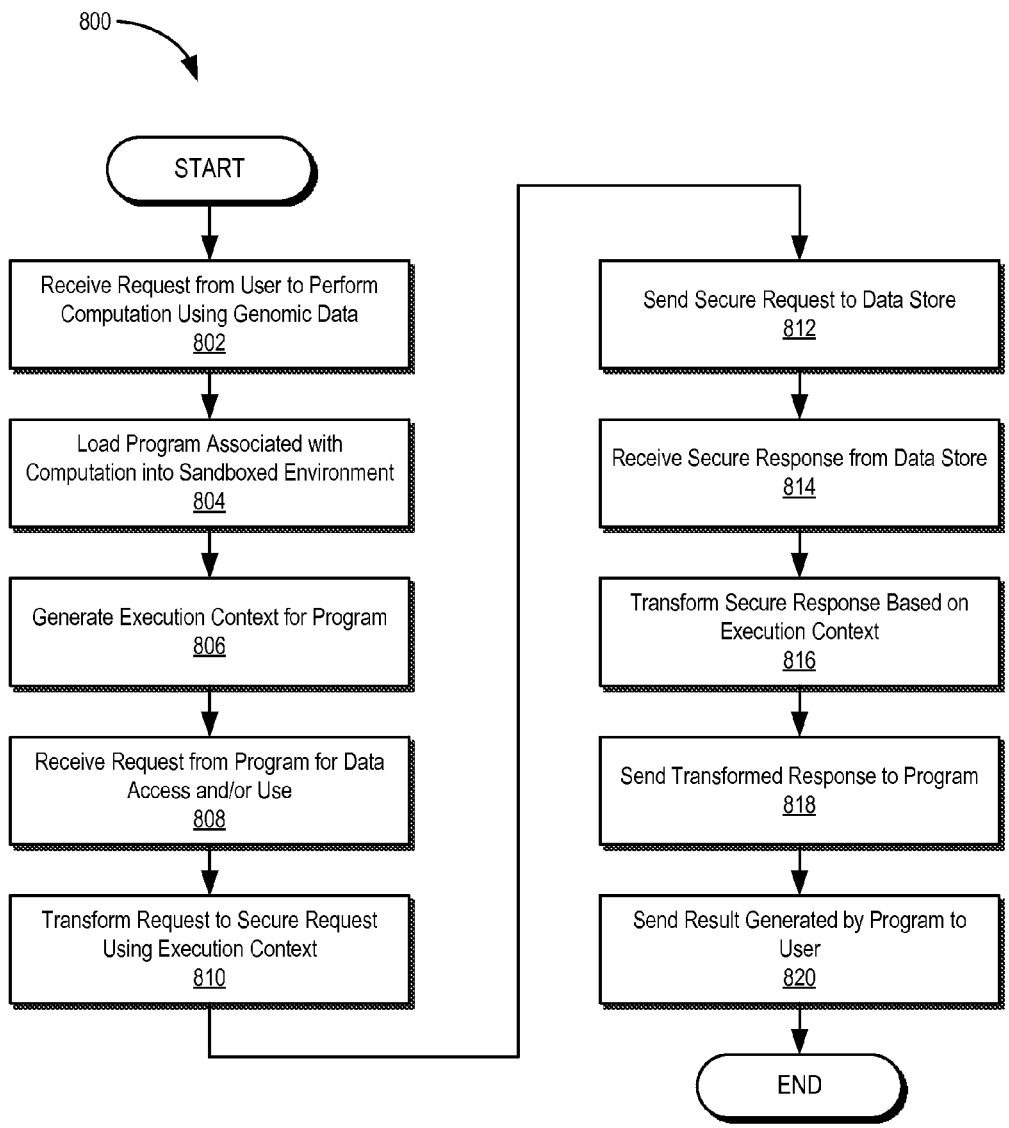
FIG. 8 illustrates a flow chart of an exemplary method of interacting with sensitive data consistent with embodiments disclosed herein.

FIG. 8 illustrates a flow chart of an exemplary method 800 of interacting with genomic or other sensitive data consistent with embodiments disclosed herein. The illustrated method 800 may be implemented in a variety of ways, including using software, firmware, hardware, and/or any other combination thereof. In certain embodiments, the method 800 and/or any of its constituent steps may be performed by a system implementing a data service consistent with certain disclosed embodiments.

At 802, a request may be received from a user to perform a computation using a genomic data set. In some embodiments, the request may be received by an execution manager executing on a system implementing certain embodiments of the disclosed genomic data service. The request may, for example, comprise a request to access the genomic data set and/or a request for a result of a computation based on a genomic data set.

In response to receiving the request, at 804, one or more programs associated with the requested computation may be loaded into one or more virtualized and/or otherwise sandboxed or limited execution environments. In some embodiments, the one or more virtualized execution environments may be initialized in response to receiving the original request from the user. In further embodiments, the one or more virtualized execution environments may be associated with different address space(s) from a data store configured to manage the genomic data set.

An execution context and/or multiple execution contexts for the one or more programs may be generated by the execution manager at 806. In certain embodiments, the execution context(s) may comprise a mapping between a set of actual identifiers associated with the genomic data set and a set of ephemeral identifiers provided to requesting programs. These identifiers may be generated in a variety of ways including, for example, randomly and/or based on a difficult-to-invert function (e.g., an encryption function, a hashing function, etc.).

At 808, request(s) from the program(s) for access to and/or use of the genomic data set may be received by a data access proxy module executing on the system. Using the execution context(s), the data access proxy module may generate and/or otherwise transform the request(s) into secure data request(s) at 810. In further embodiments, one or more identified policies may be used in connection with generating the secure data request(s) (e.g., policies associated with the genomic data set, the requesting user, and/or the requesting program(s)).

The generated secure data request(s) may be sent by the data access proxy module to a data store managing the genomic data set at 812. At 814, the data access proxy module may receive a secure data response(s) from the data store in response to the secure data request(s). Based on the execution context(s) and/or identified policies, the data access proxy module may transform the secure response at 816 and may provide the transformed response 818 to the program(s) executing in the virtualized execution environment(s). A response to the user's original request generated by the one or more program(s) based on information received from the data access proxy module may be sent to the user at 820.

Figure 9:
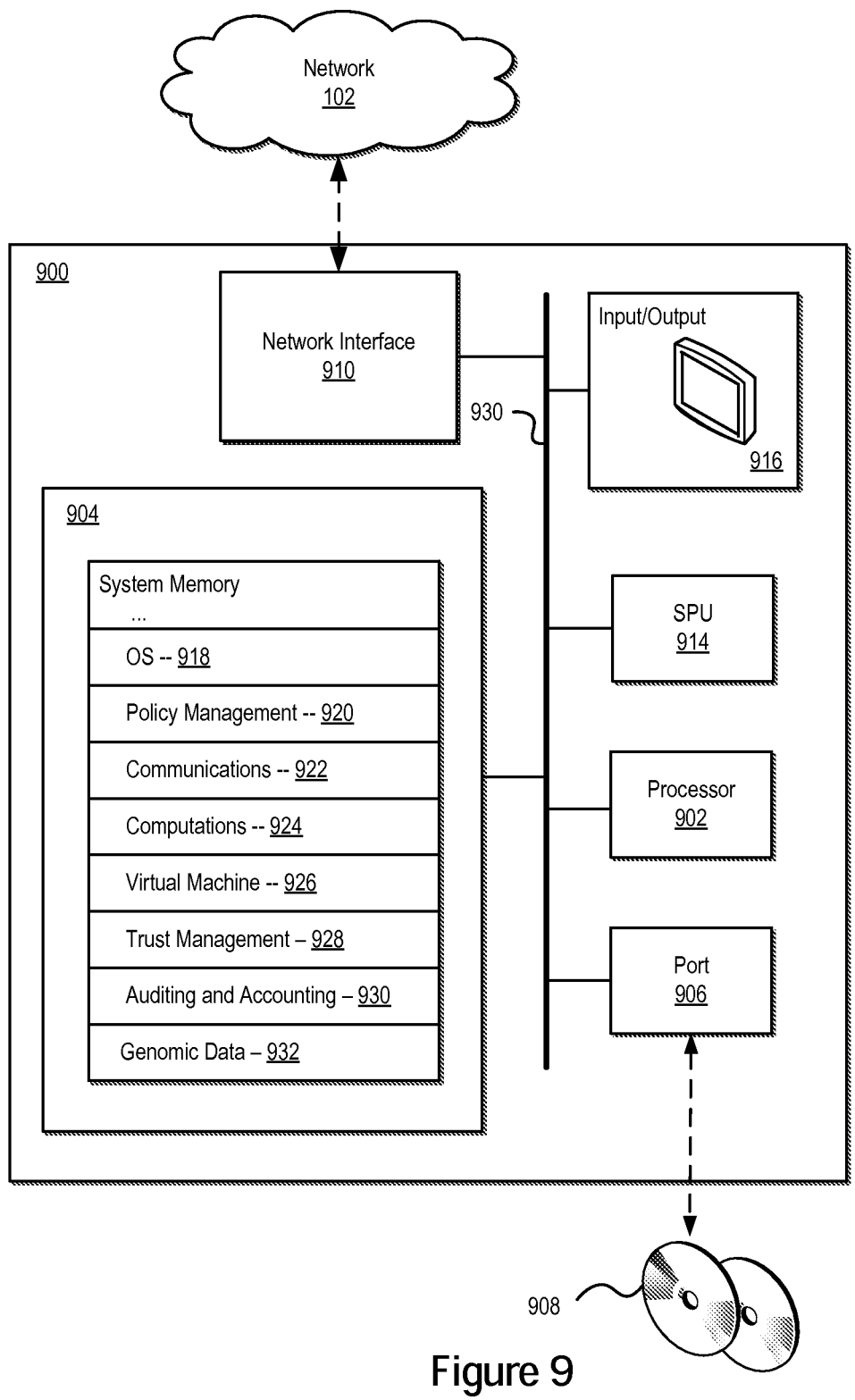
FIG. 9 illustrates an exemplary system that may be used to implement embodiments of the systems and methods disclosed herein.

FIG. 9 illustrates an exemplary system 900 that may be used to implement embodiments of the systems and methods disclosed herein. The exemplary system 900 may comprise a device and/or a computer system that may perform the operations disclosed herein. For example, system 900 may comprise at least part of a genomic data storage and/or processing system configured to implement a genomic data service consistent with the disclosed systems and methods.

As illustrated in FIG. 9, the system 900 may include: a processing unit 902; system memory 904, which may include high speed random access memory ("RAM"), non-volatile memory ("ROM"), and/or one or more bulk non-volatile computer-readable storage mediums (e.g., a hard disk, flash memory, etc.) for storing programs and other data for use and execution by the processing unit 902; a port 906 for interfacing with removable memory 908 that may include one or more diskettes, optical storage mediums (e.g., flash memory, thumb drives, USB dongles, compact discs, DVDs, etc.) and/or other computer-readable storage mediums; a network interface 910 for communicating with other systems via one or more network connections 102 using one or more communication technologies (e.g., communicating with one or more client systems and/or remote data stores); a user interface 916 that may include a display and/or one or more input/output devices such as, for example, a touchscreen, a keyboard, a mouse, a track pad, and the like; and one or more busses 930 for communicatively coupling the elements of the system 900.

In some embodiments, the system 900 may, alternatively or in addition, include an SPU 914 that is protected from tampering by a user of system 914 or other entities by utilizing secure physical and/or virtual security techniques. An SPU 914 can help enhance the security of sensitive operations such as trusted credential and/or key management, secure genomic data management, and other aspects of the systems and methods disclosed herein. In certain embodiments, the SPU 914 may operate in a logically secure processing domain and be configured to protect and operate on sensitive information. In some embodiments, the SPU 914 may include internal memory storing executable instructions or programs configured to enable the SPU 914 to perform secure operations. In further embodiments, the SPU 914 may be used to implement a protected execution environment for performing computations on genomic data as described herein. For example, in some embodiments an SPU 914 such as described in commonly-assigned U.S. Pat. No. 7,430,585 ("the '585 patent") and/or U.S. Pat. No. 5,892,900 ("the '900 patent") could be used.

The operation of the system 900 may be generally controlled by a processing unit 902 and/or a SPU 914 operating by executing software instructions and programs stored in the system memory 904 (and/or other non-transitory computer-readable media, such as removable memory 908). The system memory 904 may store a variety of executable programs or modules for controlling the operation of the system 900. For example, the system memory 904 may include an operating system ("OS") 918 that may manage and coordinate, at least in part, system hardware resources and provide for common services for execution of various applications and a policy management module 920 configured to manage and/or enforce policy associated with genomic and/or other sensitive data. The system memory 904 may further include, without limitation, communication software 922 configured to enable in part communication within and by the system 900, computations 924 (e.g., programs, computations, and/or applications configured to operate on genomic data or the like that, in some circumstances, may be untrusted), a virtual machine module 926 configured to implement generation of a virtualized and/or otherwise protected and/or sandboxed execution environment and/or machine consistent with embodiments disclosed herein, a trust management module 928 configured to implement embodiments of the disclosed trust management processes, an auditing and accounting module 930 configured to implement auditing and/or accounting processes consistent with the disclosed embodiments, and/or locally stored genomic data 932.

The systems and methods disclosed herein are not inherently related to any particular computer, electronic control unit, or other apparatus and may be implemented by a suitable combination of hardware, software, and/or firmware. Software implementations may include one or more computer programs comprising executable code/instructions that, when executed by a processor of a computer system, may cause the computer system to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network. Software embodiments may be implemented as a computer program product that comprises a non-transitory storage medium configured to store computer programs and instructions, that when executed by a processor of a computer system, are configured to cause the computer system to perform a method according to the instructions. In certain embodiments, the non-transitory storage medium may take any form capable of storing processor-readable instructions on a non-transitory storage medium. A non-transitory storage medium may be embodied by a compact disk, digital-video disk, a magnetic tape, a magnetic disk, flash memory, integrated circuits, or any other non-transitory memory device.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein, but may be modified within the scope and equivalents of the appended claims.

What is claimed is:

1. A method for performing trusted computations on sensitive data performed by a system comprising a processor and a non-transitory computer-readable storage medium storing instructions that, when executed by the processor, cause the system to perform the method, the method comprising:

receiving, by an execution manager executing on the system, a request from a user to perform a computation using a genomic data set;

loading a first program associated with the computation within a first virtualized execution environment executing on the system;

generating, by the execution manager, first execution context for the first program;

receiving, by a data access proxy module executing on the system, a first data request from the first program to use the genomic data set;

generating, by the data access proxy module, a first secure data request based on the first data request and the first execution context;

sending, by the data access proxy module to a data store managing the genomic data set, the first secure data request, receiving, by the data access proxy module from the data store, a first secure data response based on the first secure data request;

generating, by the data access proxy module, a first response to the first data request by transforming the first secure data response based on the first execution context; and sending, by the data access proxy module to the first program, the first response to the first data request.

2. The method of claim 1, wherein the method further comprises:

sending, by the execution manager, a response to the request from the user generated based on the first response.

3. The method of claim 1, wherein the method further comprises:

initializing, in response to receiving the request from the user, the first virtualized execution environment.

4. The method of claim 1, wherein the method further comprises:

identifying, by the data access proxy module, a policy associated with the first data request, wherein the secure data request is further generated based on the identified policy.

5. The method of claim 4, wherein the policy is identified based on the first program.

6. The method of claim 4, wherein the policy is identified based on the genomic data set.

7. The method of claim 4, wherein the policy is identified based on an identity of the user.

8. The method of claim 1, wherein the first virtualized execution environment comprises a limited execution environment.

9. The method of claim 8, wherein the first virtualized execution environment is associated with a different address space than the data store.

10. The method of claim 1, wherein the data store comprises a local data store.

11. The method of claim 1, wherein the data store comprises a distributed data store.

12. The method of claim 1, wherein the first data request comprises a request to access the genomic data set.

13. The method of claim 1, wherein the first data request comprises a request for a result generated based on the genomic data set.

14. The method of claim 1, wherein the method further comprises:

loading a second program associated with the computation within a second virtualized execution environment executing on the system;

generating, by the execution manager, second execution context for the second program;

receiving, by the data access proxy module executing on the system, a second data request from the second program to use the genomic data set;

generating, by the data access proxy module, a second secure data request generated based on the second execution context; and sending, by the data access proxy module to the data store, the second secure data request.

15. The method of claim 14, wherein the method further comprises:

receiving, by the data access proxy module from the data store, a second secure data response based on the second secure data request; and sending, to the second program by the data access proxy module, a second response to the second data request generated based on the second secure data response and the second execution context, wherein the response to the request from the user is further generated based on the second response.

16. The method of claim 1, wherein the first execution context comprises a mapping between a first set of identifiers and a second set of identifiers.

17. The method of claim 16, wherein the first set of identifiers comprises protected actual identifiers associated with the genomic data set and the second set of identifiers comprises ephemeral identifiers accessible by the first program and the second program.

18. The method of claim 17, wherein the second set of identifiers are generated randomly.

19. The method of claim 18, wherein the second set of identifiers are generated by a applying a function to the first set of identifiers.

20. The method of claim 19, wherein the function comprises at least one of an encryption function and a hashing function.

* * * * *